United States Patent
Hannant et al.

[11] Patent Number: 5,390,382
[45] Date of Patent: Feb. 21, 1995

[54] PATIENT SUPPORT TABLES AND MONITORS

[75] Inventors: Keith Hannant, Rustington; John A. Gardner, Steyning, both of England

[73] Assignee: Smiths Industries Public Limited Company, London, England

[21] Appl. No.: 971,465

[22] Filed: Nov. 4, 1992

[30] Foreign Application Priority Data

Nov. 28, 1991 [GB] United Kingdom ............. 9125280

[51] Int. Cl.⁶ ..................... A61G 7/00; H02H 3/00
[52] U.S. Cl. ............................. 5/424; 5/600; 361/42; 361/86
[58] Field of Search .......... 5/600, 424; 361/42, 361/86, 45, 46, 54, 88, 15, 17

[56] References Cited

U.S. PATENT DOCUMENTS

| | | | |
|---|---|---|---|
| 3,590,322 | 1/1971 | Carr | 361/42 |
| 3,845,355 | 10/1974 | Lawson | 5/424 |
| 3,978,465 | 8/1976 | Goode | 361/42 |
| 4,122,854 | 10/1978 | Blackett | 361/42 |
| 4,200,104 | 4/1980 | Harris | 361/42 |
| 4,200,105 | 4/1980 | Gonser | |
| 4,231,372 | 11/1980 | Newton | |
| 4,558,309 | 12/1985 | Antonevich | 361/42 |
| 4,580,186 | 4/1986 | Parker | 361/42 |
| 4,716,487 | 12/1987 | Horvath et al. | 361/42 |

FOREIGN PATENT DOCUMENTS

| | | |
|---|---|---|
| 0138157 | 4/1985 | European Pat. Off. . |
| 3610393 | 10/1986 | Germany . |
| 8603350 | 6/1986 | WIPO . |

*Primary Examiner*—Flemming Saether
*Attorney, Agent, or Firm*—Pollock, VandeSande and Priddy

[57] ABSTRACT

An operating table used with electrosurgery equipment has a high impedance static discharge resistor connected between the table and ground. A monitor is connected across the resistor and is responsive to a change in resistance between the table and ground which is indicative of bypassing or failure of the resistor and which is independent of operation of the electrosurgery equipment. The monitor provides an output to an alarm and also disables the electrosurgery equipment in response to such a change in resistance.

9 Claims, 1 Drawing Sheet 5,390,382

PATIENT SUPPORT TABLES AND MONITORS

BACKGROUND OF THE INVENTION

This invention relates to systems including patient support tables and monitors.

Surgical operating tables and the like are often used in conjunction with electrical equipment such as electrosurgery equipment. In order to reduce the risk of electrocution of the patient, the table is usually electrically isolated from ground, apart from a static discharge path provided through a high impedance resistor of about 100K$\Omega$ connected in series between the table and ground. If, however, ground object is inadvertently placed in contact with the table or the patient, this provides a low impedance ground leakage path which bypasses the resistor. This can put the patient at risk if he should come into contact with a live conductor.

BRIEF SUMMARY OF THE INVENTION

It is an object of the present invention to provide a system including a table and monitor which can be used to reduce the risk of danger to the patient.

According to one aspect of the present invention there is provided a system including a patient support table which is normally electrically-isolated from ground except for a high impedance static discharge resistor connected in series between the table and ground, the system including a monitor connected across the resistor and the monitor being responsive to change in resistance between the table and ground and providing an output in accordance therewith.

The monitor may include a capacitor, means for charging the capacitor, means for periodically connecting the capacitor across the resistor and a means for detecting the decay rate of the capacitor through the resistor, the detecting means being responsive to a change in the decay rate and providing an output in accordance therewith.

Alternatively, the monitor may include a transformer, the primary winding of the transformer being connected to a source of alternating voltage and the secondary winding being connected across the resistor, the monitor including means for detecting change in voltage across the primary winding indicative of change in resistance between the table and ground and for providing an output in accordance therewith.

The system may include an alarm unit, the output being provided to an alarm unit to provide an audible or visual warning. The system may include an electrosurgery unit, the output being provided to the electrosurgery unit to disable the electrosurgery unit. The monitor may be incorporated in the table or connected to the table by a cable.

According to another aspect of the present invention there is provided a monitor for a system according to the above one aspect of the invention.

A system including an operating table and a monitor, in accordance with the present invention, will now be described, by way of example, with reference to the accompanying drawings.

DETAILED DESCRIPTION OF THE PREFERRED EMBODIMENTS

Figure 1:
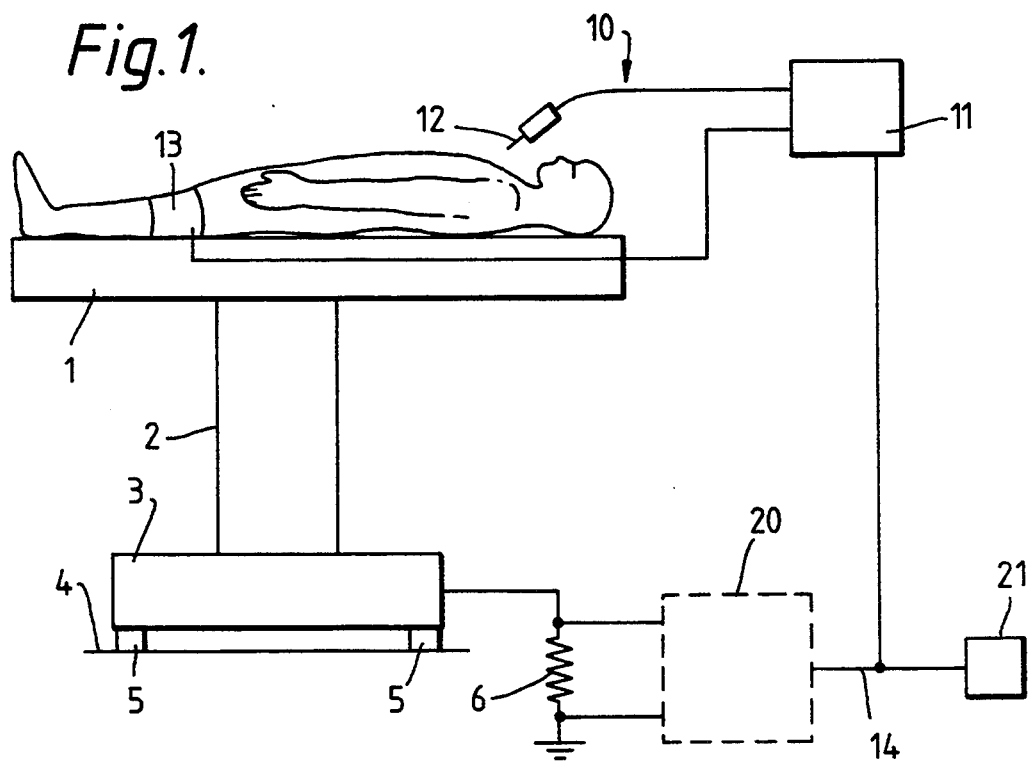
FIG. 1 illustrates the system in use with electrosurgery apparatus.

With reference to FIG. 1, the table includes a conventional patient support platform 1 at the upper end of an adjustable column 2 which is mounted on a base 3. The base 3 stands on the floor 4 on four electrically-insulative feet 5, such as of rubber, or on insulating castors or wheels (not shown). The table is made mainly of metal and it is, therefore, electrically conductive but is isolated from ground by the feet 5. In order to discharge static that may build up on the table, a high impedance resistor 6 is connected between ground and the base 3 or some other part of the table. The impedance of the resistor 6 is 100K$\Omega$ such that current flow through it is limited to values that are safe to the patient in the event that a live conductor should come into contact with the patient or table.

The table may be used in conjunction with electrosurgery equipment 10 forming a part of the system. This equipment comprises an electrosurgery generator 11 that produces RF current to a hand-held electrode 12 which is applied by the surgeon to the patient's tissue so as to effect cutting, coagulation or a combination of cutting and coagulation. A return current path to the generator 11 is provided via a large area plate electrode 13 attached to a part of the patient.

As so far described, the system is conventional.

The system differs from previous systems, however, in that it includes a monitor 20 connected across the resistor 6 which detects change in resistance between the table and ground; the monitor responds to such a change by providing an output on line 14 to an alarm unit 21, and, or alternatively, to the electrosurgery generator 11. The alarm unit 21 provides a visual or audible alarm, or both, to alert the user that isolation of the table has been compromised. The output provided to the electrosurgery generator 11 could be arranged to disable the generator and terminate supply of power. It is preferable that an alarm is also given since there are often other electrical equipment in the vicinity of the table, such as electrically-operated instruments, monitors, lights and the like which, if faulty, could lead to a live conductor coming into contact with the patient or table.

Figure 2:
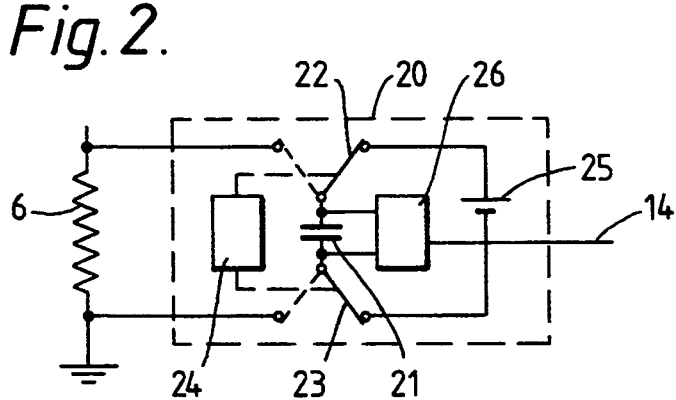
FIG. 2 is a circuit diagram of one form of monitor.
Figure 3:
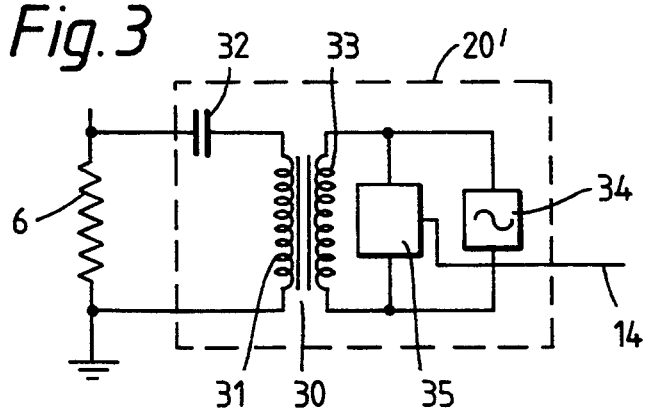
FIG. 3 is a circuit diagram of an alternative form of monitor.

The monitor 20 may take several different forms, two of which are illustrated in FIGS. 2 and 3 respectively.

With reference first to FIG. 2, the monitor 20 has a capacitor 21 the electrodes of which are connected to respective change-over switches 22 and 23. Although illustrated as being mechanical devices, the switches 22 and 23 would in practice be conventional electronic switches controlled by a switching unit 24. With the switches 22 and 23 in the position illustrated, the capacitor 21 is connected across a battery 25, or other dc voltage source, so that the capacitor is charged. When the position of the switches 22 and 23 changes to that shown in broken lines, the capacitor 21 is instead connected across the resistor 6. In this position, the charge on the capacitor 21 is dissipated through the resistor 6. The monitor 20 also includes a voltage measuring unit 26 connected across the capacitor 21 which measures the rate of decay of charge from the capacitor when it is connected across the resistor 6. If there is an alternative path to ground in addition to the resistor 6, there will be a reduction in the time taken for the charge on the capacitor to decay to a set voltage. This reduction in decay time is detected by the unit 26 which provides an output on line 14 to the alarm unit 21 and, or alternatively, to the electrosurgery generator 11. Similarly, if the resistor 6 should fail open circuit, this would lead to an increase in the decay time which is also detected by the unit 26 and signalled to the user by an appropriate alarm.

FIG. 3 shows an alternative monitor 20' which includes a transformer 30 having a secondary winding 31 connected across the resistor 6 via an isolating capacitor 32. The primary winding 33 of the transformer 30 is connected to a source 34 of high frequency voltage. A voltage measuring unit 35 is connected across the primary winding 33. If an alternative path to ground exists, apart from the resistor 6, the secondary winding 31 will be short circuited, thereby causing the voltage on the primary winding 33 to reduce. The voltage measuring unit 35 detects any such change in voltage on the primary winding and provides an output on line 14 accordingly to the alarm unit 21 and, or alternatively, to the electrosurgery generator 11.

The resistor 6 and monitor 20 may, for example, be incorporated within the base 3 of the table or they may be connected to the table by a cable.

It will be appreciated that various other forms of monitor could be used which are capable of responding to change in resistance between the table and ground.

We claim:

1. A system comprising: a patient support table; an electrosurgery unit; means normally electrically-isolating the table from ground; a high impedance static discharge resistor connected in series between the table and ground; a monitor connected across the resistor, said monitor including a power supply, and said monitor being responsive to a reduction in resistance between the table and ground independent of the operation of said electrosurgery unit, and providing an output in accordance with said reduction in resistance.

2. A system according to claim 1, wherein the monitor includes a capacitor, means for charging the capacitor, means for periodically connecting the capacitor across the resistor and means for detecting the decay rate of the capacitor through the resistor, and wherein the detecting means is responsive to a change in the decay rate and provides said output in accordance therewith.

3. A system according to claim 1, wherein the monitor includes a source of alternating voltage; a transformer having a primary winding and a secondary winding; means connecting the primary winding to the source of alternating voltage; means connecting the secondary winding to said resistor; and means for detecting a change in voltage across the primary winding indicative of a fall in resistance between the table and ground and for providing the output in accordance therewith.

4. A system according to claim 1 or 2, including an alarm unit, and means supplying the output of said monitor to the alarm unit to pro,de an audible or visual warning.

5. A system according to claim 1 or 2, including a connection supplying the output of said monitor to the electrosurgery unit to disable the electrosurgery unit.

6. A system according to claim 1, wherein the monitor is incorporated in the table.

7. A system according to claim 1, including a cable connected between the monitor and the table.

8. A system comprising a patient support table; an electrosurgery unit; means normally electrically-isolating the table from ground; a high impedance static discharge resistor connected in series between the table and ground; an alarm unit; a monitor connected across the resistor, wherein the monitor includes a capacitor, a voltage source, means connecting the voltage source to the capacitor to charge the capacitor, and a detector for detecting the decay rate of the capacitor charge through the resistor, the detector being responsive to a change in decay rate independent of the operation of said electrosurgery unit and providing an output to the alarm unit in accordance therewith.

9. A system comprising: a patient support table; an electrosurgery unit; means normally electrically-isolating the table from ground; a high impedance static discharge resistor connected in series between the table and ground; an alarm unit; a monitor connected across the resistor, wherein the monitor includes a source of alternating voltage and a transformer, the transformer having a primary winding and a secondary winding; means connecting the primary winding to the source of alternating voltage, means connecting the secondary winding across said resistor, and a detector for detecting a change in voltage across the primary winding indicative of a change in resistance between the table and ground independent of the operation of said electrosurgery unit and for providing an output to the alarm unit in accordance therewith.

* * * * *